United States Patent [19]

Nair et al.

[11] 4,342,752
[45] Aug. 3, 1982

[54] CARBALKOXYMETHYL DERIVATIVES OF RUTIN POLY(H-)SULFATE AND METHOD OF USE

[75] Inventors: Vijay G. Nair, New York; John F. Poletto, Nanuet; Seymour Bernstein, New City, all of N.Y.

[73] Assignee: American Cyanamid Company, Stamford, Conn.

[21] Appl. No.: 273,523

[22] Filed: Jun. 15, 1981

[51] Int. Cl.$^3$ .................... A61K 31/70; C07H 13/04
[52] U.S. Cl. ........................... 424/180; 424/49; 424/56; 536/8; 536/118; 536/119
[58] Field of Search ............... 424/180; 536/8, 118

[56] References Cited

U.S. PATENT DOCUMENTS

| | | | |
|---|---|---|---|
| 4,021,544 | 5/1977 | Nair et al. | 536/118 |
| 4,021,545 | 5/1977 | Nair et al. | 536/118 |
| 4,098,995 | 7/1978 | Nair et al. | 536/118 |
| 4,153,788 | 5/1979 | Courbat et al. | 536/8 |

*Primary Examiner*—Johnnie R. Brown
*Attorney, Agent, or Firm*—Barbara A. Shimei

[57] ABSTRACT

Carbalkoxymethyl derivatives of rutin poly(H-)sulfate and salts thereof useful as complement inhibitors.

19 Claims, No Drawings

CARBALKOXYMETHYL DERIVATIVES OF RUTIN POLY(H-)SULFATE AND METHOD OF USE

BACKGROUND OF THE INVENTION

1. Field of Invention

The present invention relates to novel carbalkoxymethyl derivatives of rutin poly(H-)sulfates and salts thereof and their use as inhibitors of the complement system of warm-blooded animals, and to novel intermediates for their preparation.

2. Description of the Prior Art

Certain sulfated polysaccharides have been reported as having complement inhibiting activity, for example, heparin, J. Infect. Dis. 44: 250–253 (1929); carrageenin, Immunology 8: 291 (1965); and pentosan polysulfoester, Chemical Abstracts 75: 33179s (1971). The basic rutin poly(H-)sulfates and salts thereof are the subject of application Ser. No. 181,251, filed Aug. 25, 1980 and its parent applications Ser. No. 62,587, filed July 31, 1979, now abandoned, and Ser. No. 966,423, filed Dec. 4, 1978, now abandoned, all incorporated herein by reference. However, no art is known which discloses anticomplementary activity for the novel carbalkoxymethyl derivatives of rutin poly(H-)sulfate which are the subject of this invention.

A rutin sulfate sodium salt ("rutin water soluble") is commercially available from E. Merck, Darmstadt, West Germany, Catalogue No. 5000014. This material, which is useful as an injectable form of Vitamin P, has an analysis, S=5.45%. "Rutin water soluble" has been tested for complement inhibiting activity, using the tests disclosed herein, and has been found lacking in complement inhibiting activity. Sulfation of "rutin water soluble" produces the rutin poly(H-)sulfates of the aforementioned United States patent applications, (sulfur analysis S=16.5%) which are active as complement inhibitors.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds, 3,3'-ureylenebis[6-(2-amino-8-hydroxy-6-sulfo-1-naphthylazo) benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochem. Biophys. Acta 317: 539 (1973); Life Sci. 13: 351 (1973); J. Immunol. 113: 584 (1974); Immunology 26: 819 (1974); J. Med. Chem. 17: 1160 (1974); Biochem. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochem. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

It has now been discovered that carbalkoxymethyl derivatives of rutin poly(H-)sulfates interact with the complement reaction sequence, thereby inhibiting complement activity in body fluids.

This invention is particularly concerned with the pharmaceutically acceptable salts of carbalkoxymethyl derivatives of rutin poly(H-)sulfate, having complement activity of the formula (I):

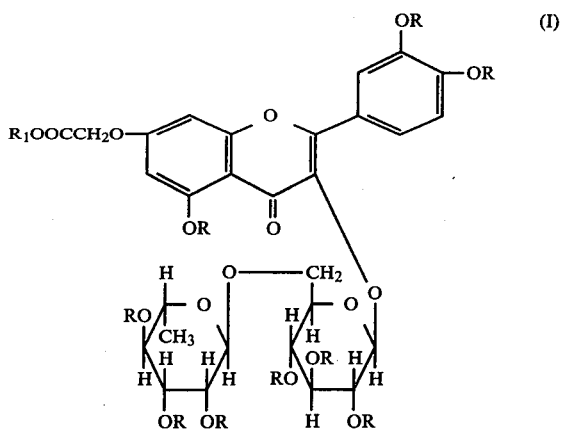

wherein $R_1$ is $C_1-C_6$ alkyl, R is $SO_3B$, and B is a pharmaceutically acceptable salt cation, wherein the salt forming moiety is selected from the group alkali metal, alkaline earth metal, ammonia and substituted ammonia selected from the group $C_1-C_6$ trialkylamine, piperidine, pyrazine, $C_2-C_6$ alkanolamine, and $C_3-C_6$ cycloalkylamine.

This invention is also concerned with a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention is further concerned with a method of inhibiting the complement system in a warm-blooded animal which comprises administering to said animal an effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as for example, inflammation following coronary occlusion. They may also be useful in the treatment of transplant rejection and ulcers and as blood culture and transport mediums.

This invention is further concerned with compounds of the formula (II):

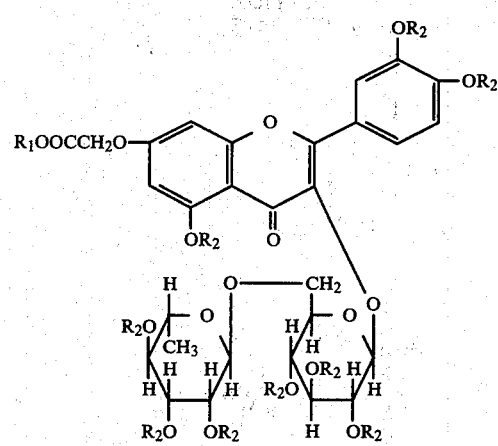

(II)

wherein $R_1$ is as defined above and $R_2$ is selected from the group —COCH$_3$ and —OH. These compounds are useful as intermediates for the preparation of the compounds of Formula I.

DESCRIPTION OF THE PREFERRED EMBODIMENTS

The compounds of the present invention which are useful as complement inhibitors are those represented by the following generic formula:

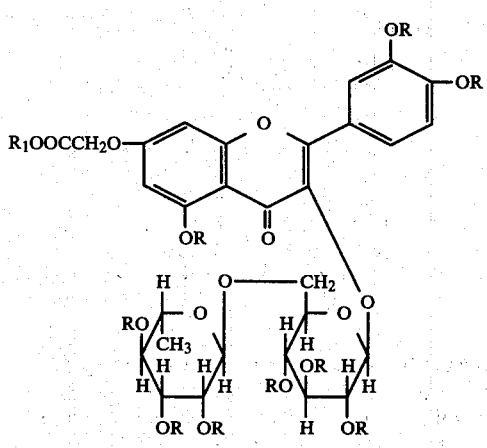

(I)

wherein $R_1$ is $C_1$-$C_6$ alkyl, R is SO$_3$B, and B is a pharmaceutically acceptable salt cation, wherein the salt forming moiety is selected from the group alkali metal, alkaline earth metal, ammonia and substituted ammonia selected from the group $C_1$-$C_6$ trialkylamine, piperidine, pyrazine, $C_2$-$C_6$ alkanolamine and $C_3$-$C_6$ cycloalkylamine.

Preferably, B is an alkali metal cation.

A particularly preferred compound of this invention which is of major interest as a complement inhibitor is given below, followed by its Chemical Abstracts nomenclature:

7-O-carbethoxymethyl-rutin nona(H-)sulfate)sodium salt [2-(3,4-dihydroxyphenyl)-3,5-dihydroxy-4-oxo-4H-1-benzopyran-7-yloxy], acetic acid, ethyl ester 3-[6-O-(6-deoxy-alpha-L-mannopyranosyl)-beta-D-glucopyranoside], nonakis(H-sulfate), nonasodium salt Compounds of the present invention which are useful as intermediates in the preparation of the compounds of Formula I are those represented by the following generic formula:

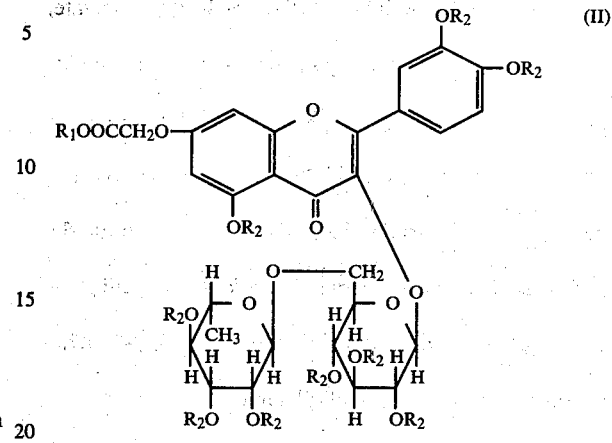

(II)

wherein $R_1$ is defined above and $R_2$ is selected from the group —COCH$_3$ and —OH.

Particularly preferred compounds of Formula II are:
7-O-carbethoxymethyl-rutin nonaacetate [2-(3,4-dihydroxyphenyl)-3,5-dihydroxy-4-oxo-4H-1-benzopyran-7-yloxy], acetic acid, ethyl ester 3-[6-O-(6-deoxy-alpha-L-mannopyranosyl-beta-D-glucopyranoside]-nonaacetate 7-O-carbethoxymethyl-rutin [2-(3,4-dihydroxyphenyl)-3,5-dihydroxy-4-oxo-4H-1-benzopyran-7-yloxy], acetic acid, ethyl ester 3-[6-O-(6-deoxy-alpha-L-mannopyranosyl-beta-D-glucopyranoside]

The rutin poly(H-)sulfate salts which are the precursors of the compounds of Formula II may be prepared by the application or adaption of known methods, for example, as described in Chemical Reviews 62: 549–589 (1962); and U.S. Pat. Nos. 3,271,388; 2,923,704; 2,686,779; and 2,697,093; or as described hereinbelow. These known intermediates are then used in the preparation of the compounds of this invention.

The compounds of the present invention are prepared as described in Flowchart A.

In accordance with Flowchart A, rutin decaacetate (1) is reacted with an alkyl chloroacetate ($R_1$=$C_1$-$C_6$ alkyl), an acid scavenger such as for example potassium or sodium carbonate, and optionally potassium or sodium iodide, in an aqueous dialkylketone solvent such as, e.g., diethylketone, methylethylketone, etc. for 24–48 hours, giving 7-O-carbalkoxymethyl-rutin nonaacetate (2) which is recovered by hexane precipitation from an ether solution. The compound (2) is then converted to 7-O-carbalkoxymethylrutin (3) by treatment with triethylamine in aqueous alkanol (such as, e.g., methanol) for 16–30 hours. The compound (3) is then treated with a $C_1$-$C_6$ trialkylamine (preferably triethylamine)-sulfur trioxide composition in a solution of a solvent such as dimethylformamide (DMF) or N,N-dimethylacetamide (DMA). The solution may additionally contain a drying agent such as calcium sulfate. Typically, the reaction proceeds at 50°–75° C. for 2–4 hours, after which the rutin-trialkylammonium salt is separated. In a typical separation, the mixture is added to acetone and refrigerated, giving the carbalkoxymethyl-rutin poly(H-sulfate)trialkylammonium derivative (4) where $R_1$ is as defined above, R is SO$_3$B, and B is ($C_1$-$C_6$ alkyl)$_3$NH. The trialkylammonium derivative (4) can be treated with an aqueous solution of a water-soluble alkali or alkaline earth metal cation-containing compound (e.g., sodium acetate, potassium acetate, calcium acetate), or ammonium or a substituted ammonia selected from the group piperidine, pyrazine, $C_2$-$C_6$ alkanolamine, and $C_3$-$C_6$ cycloalkylamine, to give the carbalkoxymethyl-rutin derivative of (4) wherein $R_1$ and R are defined above and B is alkali metal, alkaline earth metal, ammonia, piperidine, pyrazine, $C_2$-$C_6$ alkanolamine, or $C_3$-$C_6$ cycloalkylamine.

FLOWCHART A

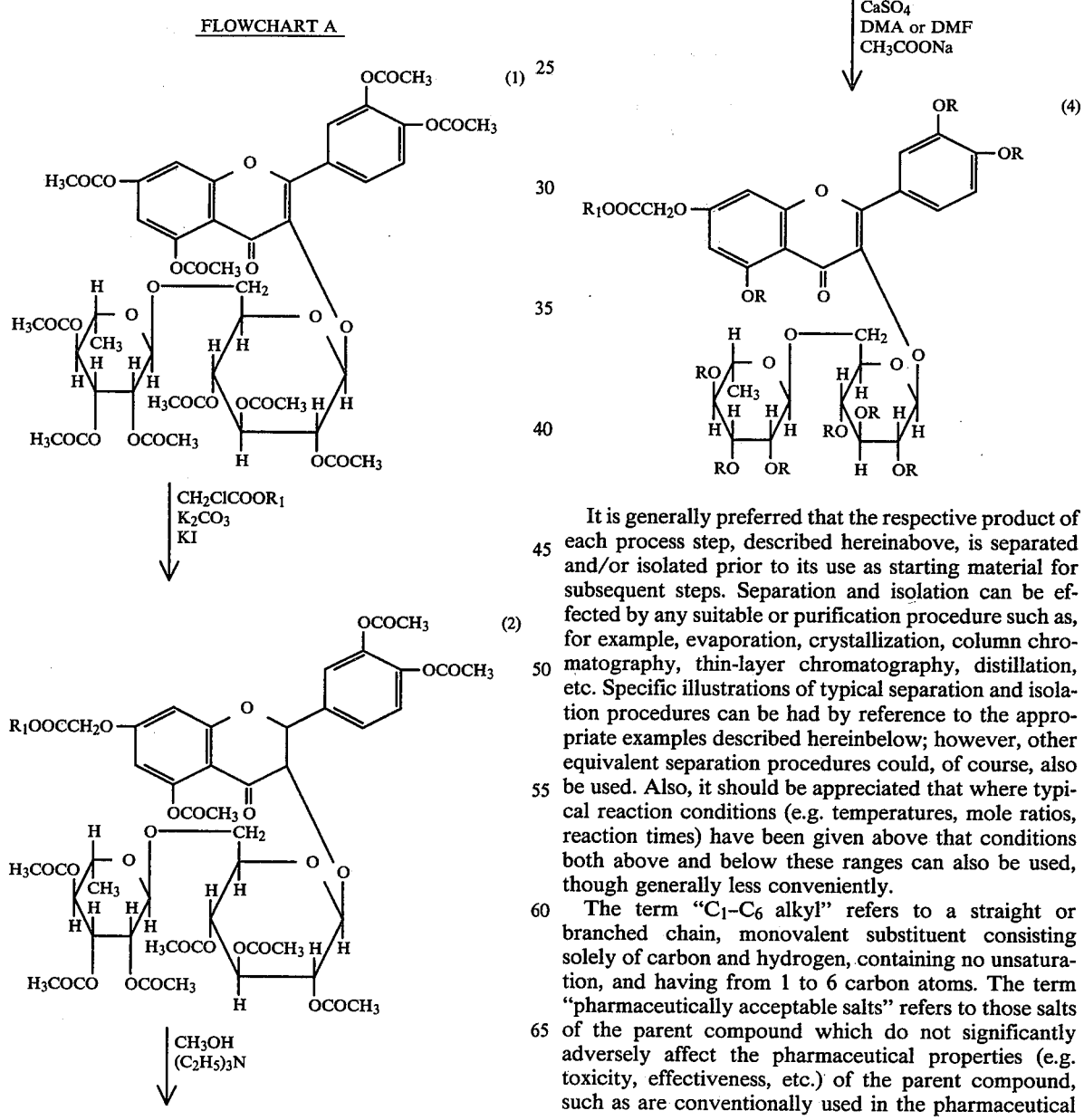

-continued
FLOWCHART A

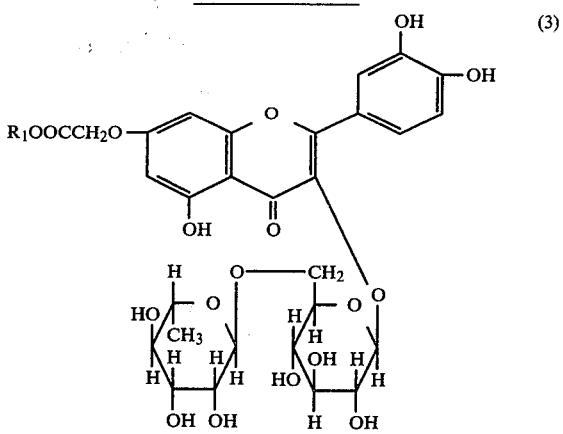

It is generally preferred that the respective product of each process step, described hereinabove, is separated and/or isolated prior to its use as starting material for subsequent steps. Separation and isolation can be effected by any suitable or purification procedure such as, for example, evaporation, crystallization, column chromatography, thin-layer chromatography, distillation, etc. Specific illustrations of typical separation and isolation procedures can be had by reference to the appropriate examples described hereinbelow; however, other equivalent separation procedures could, of course, also be used. Also, it should be appreciated that where typical reaction conditions (e.g. temperatures, mole ratios, reaction times) have been given above that conditions both above and below these ranges can also be used, though generally less conveniently.

The term "$C_1$-$C_6$ alkyl" refers to a straight or branched chain, monovalent substituent consisting solely of carbon and hydrogen, containing no unsaturation, and having from 1 to 6 carbon atoms. The term "pharmaceutically acceptable salts" refers to those salts of the parent compound which do not significantly adversely affect the pharmaceutical properties (e.g. toxicity, effectiveness, etc.) of the parent compound, such as are conventionally used in the pharmaceutical art. The salts of the present invention which are pharmaceutically acceptable include the alkali metals, e.g., sodium, potassium, etc.; alkaline earth metals, e.g. calcium, etc.; ammonia; piperidine, pyrazine; $C_1$–$C_6$ trialkylamine; $C_2$–$C_6$ alkanolamine; and $C_3$–$C_6$ cycloalkylamine.

The term "$C_1$–$C_6$ trialkylamine" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "$C_2$–$C_6$ alkanolamine" refers to the above defined trialkylamines additionally substituted with at least one and not more than three hydroxy groups on at least two of the alkyl hydrocarbon chains. Such amines are, for example, triethanolamine, tripropanolamine, etc. The term "$C_3$–$C_6$ cycloalkylamine" is defined as the 3 to 6 fully saturated carbocyclic moieties such as cyclopropyl, methylcyclobutyl, cyclopentyl, cyclohexyl, etc.

A further understanding of the invention can be had from the following non-limiting Preparations and Examples. As used hereinabove and below unless expressly stated to the contrary, all temperatures and temperature ranges refer to the centigrade system and the terms ambient or room temperature refer to about 20° C. The term percent or (%) refers to weight percent and the terms mole and moles refer to gram moles. The term equivalent refers to a quantity of reagent equal in moles to the moles of the preceding or succeeding reactant recited in the Preparation and Example in the terms of moles of finite weight or volume.

EXAMPLE 1

7-O-Carbethoxymethyl-rutin nonaacetate

A 0.25 g. portion of ethyl chloroacetate is added to a solution of 0.25 g. of rutin decaacetate, 0.30 g. of anhydrous potassium carbonate and 0.0125 g. of potassium iodide in 4 ml. of acetone. This mixture is stirred for 24 hours, then 0.124 g. of ethyl chloroacetate is added and stirring is continued for 24 hours. The mixture is filtered, the filtrate concentrated to dryness and the residue dissolved in ether. The addition of hexane causes a precipitate to form which is collected and dried, giving 200 mg. of the desired compound as a colorless powder which is characterized by standard analytical and spectroscopic procedures.

EXAMPLE 2

7-O-Carbethoxymethyl-rutin

A 1.2 g. portion of 7-O-carbethoxymethyl-rutin nonaacetate is dissolved in 24 ml. of methanol and 8 ml. of water and 12 ml. of triethylamine are added. This mixture is stirred 24 hours, filtered and the filtrate concentrated to dryness. The residue is crystallized from ethanol, giving 564 mg. of the desired compound as yellow crystals.

EXAMPLE 3

7-O-Carbethoxymethyl-rutin nona(H-sulfate)sodium salt

A 3.6 g. portion of triethylamine sulfur trioxide is dissolved in 12.5 ml. of N,N-dimethylacetamide, a 2.5 g. portion of anhydrous calcium sulfate is added and the mixture is heated at 63°–65° C. for 20 minutes. A 348 mg. portion of 7-O-carbethoxymethyl-rutin is added and this mixture is swirled and heated at 63°–65° C. for 2 hours. The reaction mixture is cooled at room temperature and filtered. The filtrate is gradually poured into 200 ml. of acetone containing 2 ml. of triethylamine. The oily product that separates is centrifuged down and the supernatant is removed by decantation. The residue is washed repeatedly with acetone, then dissolved in 1.5 ml. of water and 1.5 ml. of 30% sodium acetate solution is added. The solution is filtered and the filtrate gradually added to 300 ml. of absolute ethanol with stirring. The granular product which separates is allowed to settle, then the bulk of the supernatant is removed by decantation. The residue is recovered by filtration, washed repeatedly with ethanol followed by ether, and dried in vacuo for 18 hours, giving 215 mg. of the desired product as a yellow powder which is characterized by standard analytical and spectroscopic techniques.

EXAMPLE 4

| Preparation of Compressed Tablet | |
|---|---|
| Ingredient | mg/Tablet |
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 5

| Preparation of Compressed Tablet - Sustained Action | |
|---|---|
| Ingredient | mg/Tablet |
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 6

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 7

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 8

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 9

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 10

Preparation of Injectable Solution

| Ingredient | % W/V |
|---|---|
| Active Compound | 0.05–5 |
| Benzyl Alcohol NF | 0.9 |
| Water for Injection | 100.0 |

EXAMPLE 11

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 12

Preparation of Intra-Articular Product

| Ingredient | Amount |
|---|---|
| Active Compound | 2–20 mg |
| NaCl (physiological saline) | 0–9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 13

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |

-continued

Preparation of Injectable Depo Suspension

| Ingredient | % W/V |
|---|---|
| HCl to pH 6–8 | qs |
| Water for Injection qs ad | 100.0 |

EXAMPLE 14

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 15

Preparation of Dental Ointment

| Ingredient | % W/W |
|---|---|
| Active Compound | 0.05–5 |
| Petrolatum, White USP qs | 100 |

EXAMPLE 16

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 17

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 18

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 19

| Preparation of Spray Lotion (Non-aerosol) | |
| --- | --- |
| Ingredient | % W/W |
| Active Compound | 0.05–5 |
| Isopropyl Myristate | 20 |
| Alcohol (Denatured) qs | 100 |

EXAMPLE 20

| Preparation of Buccal Tablet | |
| --- | --- |
| Ingredient | mg/Tablet |
| Active Ingredient | 3.25 |
| 6x Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 21

| Preparation of Lozenge | |
| --- | --- |
| Ingredient | g/Lozenge |
| Active Ingredient | 0.0140 |
| Kompact ® Sugar (Sucrest Co.) | 0.7138 |
| 6x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional phamaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Cap 50 Test—Here, appropriate amounts of the test compound are added to a pool of guinea pig serum in vitro, after which the undiluted serum capillary tube assay referred to above is run. The concentration of compound inhibiting 50% is reported; and (iii) Guinea Pig Intraperitoneal Test (GPIP)—Guinea pigs weighing about 300 g. are dosed intraperitoneally (i.p.) with 200 mg./kg. of the test compound dissolved in saline and adjusted to pH 7-8. Approximately 0.4 ml. blood samples, taken by orbital sinus puncture 30 minutes and one hour after injections, are collected directly into centrifuge tubes; 5 ml. blood samples, taken by decapitation 2 hours after injection are collected directly into beakers. The samples are allowed to clot, centrifuged, and the resultant sera are assayed for complement activity using the capillary complement assay. Percent inhibition are calculated by comparison with simultaneous controls.

The results appear in Table I, which shows that the principal compound of Formula I possesses highly significant in vitro and in vivo complement inhibiting activity in warm-blooded animals.

TABLE I

| | Biological Activities | | | | |
|---|---|---|---|---|---|
| | | | In Vivo Activity (Guinea Pig) Intraperitoneal % Inhibition Time (Hours) | | |
| | In vitro Activity | | | | |
| Compound | 026* | Cap 50* | 2 | 6 | 24 |
| 7-O—Carbethoxymethyl-rutin, nona (H—sulfate)sodium salt | 12** | 67 | | | |
| | 10 | 70 | 39 | 43 | 55 |

*Code designation for tests employed as referred herein.
**Activity in wells, a serial dilution assay. Higher well number indicates higher activity. The serial dilutions are two-fold.

We claim:
1. A compound selected from those of the formula:

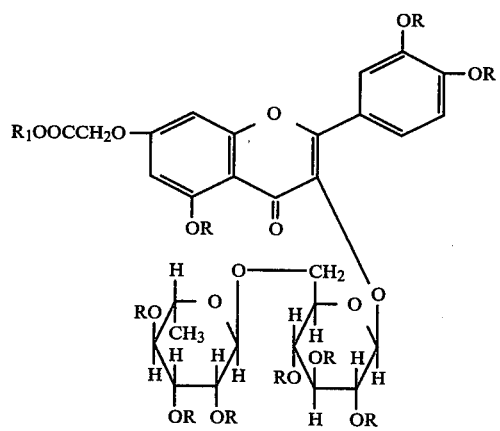

wherein $R_1$ is $C_1$-$C_6$ alkyl, R is $SO_3B$, and B is a pharmaceutically acceptable salt cation selected from the group consisting of alkali metal, alkaline earth metal, ammonia and substituted ammonia selected from the group consisting of $C_1$-$C_6$ trialkylamine, piperidine, pyrazine, $C_2$-$C_6$ alkanolamine and $C_3$-$C_6$ cycloalkylamine.

2. The compound according to claim 1, 7-O-carbethoxymethyl-rutin nona(H-sulfate)sodium salt.

3. A method of inhibiting the complement system in a body fluid which comprises subjecting said body fluid to the action of an effective complement inhibiting amount of a compound of the formula:

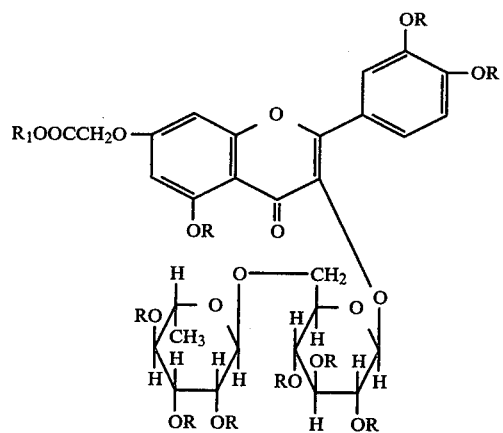

wherein $R_1$ is $C_1$-$C_6$ alkyl, R is $SO_3B$, and B is a pharmaceutically acceptable salt cation selected from the group consisting of alkali metal, alkaline earth metal, ammonia and substituted ammonia selected from the group consisting of $C_1$-$C_6$ trialkylamine, piperidine, pyrazine, $C_2$-$C_6$ alkanolamine and $C_3$-$C_6$ cycloalkylamine.

4. A method according to claim 3, wherein the compound is 7-O-carbethoxymethyl-rutin, nona(H-sulfate)-sodium salt.

5. A method of inhibiting the complement system in a warm-blooded animal which comprises administering to said animal an effective complement inhibiting amount of a compound of the formula:

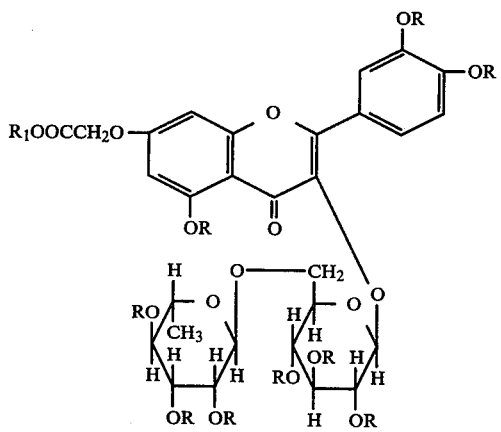

wherein $R_1$ is $C_1$-$C_6$ alkyl, R is $SO_3B$, and B is a pharmaceutically acceptable salt cation selected from the group consisting of alkali metal, alkaline earth metal, ammonia and substituted ammonia selected from the group consisting of $C_1$-$C_6$ trialkylamine, piperidine, pyrazine, $C_2$–$C_6$ alkanolamine and $C_3$–$C_6$ cycloalkylamine.

6. A method according to claim 5, wherein the compound is 7-O-carbethoxymethyl-rutin, nona(H-sulfate) sodium salt.

7. A method according to claim 5, wherein the compound is administered internally.

8. A method according to claim 5, wherein the compound is administered topically.

9. A method according to claim 5, wherein the compound is administered periodontally in the oral cavity.

10. A method according to claim 5, wherein the compound is administered intra-articularly.

11. A method according to claim 5, wherein the compound is administered parenterally.

12. A compound selected from those of the formula:

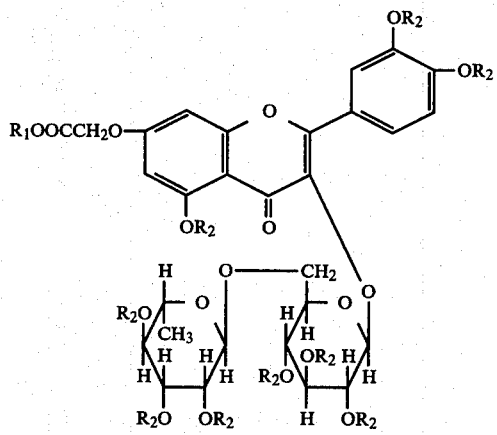

wherein $R_1$ is $C_1$–$C_6$ alkyl and $R_2$ is selected from the group consisting of —COCH$_3$ and —OH.

13. The compounds according to claim 12 wherein $R_2$ is —COCH$_3$.

14. The compounds according to claim 12 wherein $R_2$ is —OH.

15. The compound according to claim 12 or 13, 7-O-carbethoxymethyl-rutin nonaacetate.

16. The compound according to claim 12 or 14, or 7-O-carbethoxymethyl-rutin.

17. A process for the preparation of a compound of the formula:

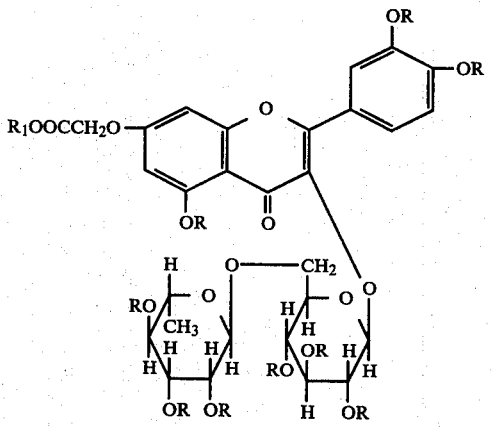

wherein $R_1$ is $C_1$–$C_6$ alkyl, R is SO$_3$B, and B is ($C_1$–$C_6$ alkyl)$_3$NH, which process comprises reacting rutin decaacetate with $C_1$–$C_6$ alkyl chloroacetate and an acid scavenger in an aqueous dialkylketone solvent for 24–48 hours, giving 7-O-carbalkoxymethyl-rutin nonaacetate wherein R is —COCH$_3$ and $R_1$ is $C_1$–$C_6$ alkyl, recovering said 7-O-carbalkoxymethyl-rutin nonaacetate by precipitation from an ether solution, converting said 7-O-carbalkoxymethyl-rutin nonaacetate to 7-O-carbalkoxymethyl-rutin wherein R is hydrogen and $R_1$ is $C_1$–$C_6$ alkyl by treatment with trimethylamine in aqueous alkanol for 16–30 hours, treating said 7-O-carbalkoxymethyl-rutin with a $C_1$–$C_6$ trialkylamine-sulfur trioxide, and separating the 7-O-carbalkoxymethyl-rutin poly(H-sulfate) trialkylammonium derivative wherein $R_1$ is $C_1$–$C_6$ alkyl, R is SO$_3$B, and B is ($C_1$–$C_6$ alkyl)$_3$NH.

18. A process for the preparation of a compound of the formula:

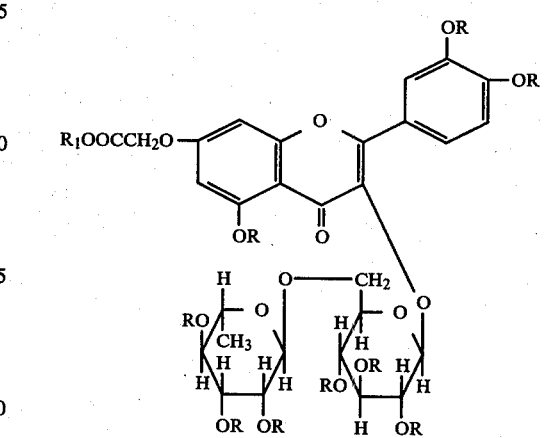

wherein $R_1$ is $C_1$–$C_6$ alkyl, R is SO$_3$B, and B is a pharmaceutically acceptable salt cation, wherein the salt forming moiety is selected from the group consisting of alkali metal, alkaline earth metal, ammonia and a substituted ammonia selected from the group consisting of $C_1$–$C_6$ trialkylamine, piperidine, pyrazine, $C_2$–$C_6$ alkanolamine and $C_3$–$C_6$ cycloalkylamine, which process comprises reacting rutin decaacetate with $C_1$–$C_6$ alkyl chloroacetate and an acid scavenger in an aqueous dialkylketone solvent for 24–48 hours, giving 7-O-carbalkoxymethyl-rutin nonaacetate wherein R is —COCH$_3$ and $R_1$ is $C_1$–$C_6$ alkyl, recovering said 7-O-carbalkoxymethyl-rutin nonaacetate by precipitation from an ether solution, converting said 7-O-carbalkoxymethyl-rutin nonaacetate to 7-O-carbalkoxymethyl-rutin wherein R is hydrogen and $R_1$ is $C_1$–$C_6$ alkyl by treatment with trimethylamine in aqueous alkanol for 16–30 hours, treating said 7-O-carbalkoxymethyl-rutin with a $C_1$–$C_6$ trialkylamine-sulfur trioxide, separating the 7-O-carbalkoxymethyl-rutin poly(H-sulfate)trialkylammonium derivative wherein $R_1$ is $C_1$–$C_6$ alkyl, R is SO$_3$B, and B is ($C_1$–$C_6$ alkyl)$_3$NH, and treating said 7-O-carbalkoxymethyl-rutin poly(H-sulfate)trialkylammonium derivative with an alkali or alkaline earth metal cation-containing compound or ammonia or substituted ammonia selected from the group consisting of piperidine, pyrazine, $C_2$–$C_6$ alkanolamine and $C_3$–$C_6$ cycloalkylamine, to yield the 7-O-carbalkoxymethyl-rutin poly(H-sulfate)salt wherein $R_1$ is $C_1$–$C_6$ alkyl, R is SO$_3$B, and B is alkali metal, alkaline earth metal, ammonia, or substituted ammonia selected from the group consisting of piperidine, pyrazine, $C_2$–$C_6$ alkanolamine, and $C_3$–$C_6$ cycloalkylamine.

19. The process according to claims 17 or 18 wherein the reaction of rutin decaacetate with $C_1$–$C_6$ alkyl chloroacetate and an acid scavenger takes place in the presence of potassium or sodium iodide.

* * * * *